US009249214B2

(12) United States Patent
Jones et al.

(10) Patent No.: US 9,249,214 B2
(45) Date of Patent: Feb. 2, 2016

(54) MONOCLONAL ANTIBODIES FOR EBOLA AND MARBURG VIRUSES

(71) Applicant: Her Majesty the Queen in the Right of Canada as Represented by the Minister of Health, Winnipeg (CA)

(72) Inventors: Steven Jones, Winnipeg (CA); Xiangguo Qiu, Winnipeg (CA); Heinz Feldmann, Winnipeg (CA); Ute Stroeher, Winnipeg (CA)

(73) Assignee: Her Majesty the Queen in the Right of Canada as Represented by the Minister of Health, Winnipeg (CA)

( * ) Notice: Subject to any disclaimer, the term of this patent is extended or adjusted under 35 U.S.C. 154(b) by 0 days.

(21) Appl. No.: 13/940,712

(22) Filed: Jul. 12, 2013

(65) Prior Publication Data

US 2015/0344546 A1    Dec. 3, 2015

Related U.S. Application Data

(62) Division of application No. 12/864,584, filed as application No. PCT/CA2009/000070 on Jan. 27, 2009, now Pat. No. 8,513,391.

(60) Provisional application No. 61/025,491, filed on Feb. 1, 2008.

(51) Int. Cl.
*C07K 16/08* (2006.01)
*C07K 16/10* (2006.01)

(52) U.S. Cl.
CPC ............. *C07K 16/10* (2013.01); *C07K 2317/21* (2013.01); *C07K 2317/56* (2013.01); *C07K 2317/62* (2013.01)

(58) Field of Classification Search
CPC .................. C07K 16/00–16/468; C07K 16/08; C07K 16/10
See application file for complete search history.

(56) References Cited

U.S. PATENT DOCUMENTS

| 8,513,391 B2 * | 8/2013 | Jones | C07K 16/10 424/130.1 |
| 2015/0232538 A1 * | 8/2015 | Jones | C07K 16/10 424/133.1 |

FOREIGN PATENT DOCUMENTS

WO    2004018649    3/2004

OTHER PUBLICATIONS

Audet et al., Scientific Reports, 4:6881 (2014), DOI: 10.1038/srep06881.*
Takada, A. et al., "Protective Efficacy of Neutralizing Antibodies Against Ebola Virus Infection", Vaccine, 2007, vol. 25, pp. 993-999, ISSN: 0264-410X.
Shahhosseini, S. et al., "Production and characterization of monoclonal antibodies against different epitopes of Ebola virus antigens", Journal of Virological Methods, 2007, vol. 143, pp. 29-37, ISSN: 0166-0934.

* cited by examiner

*Primary Examiner* — Sheela J Huff
*Assistant Examiner* — Jessica H Roark
(74) *Attorney, Agent, or Firm* — Thomas E. Jurgensen; Optima Law Group, APC

(57) ABSTRACT

Described herein are a number of Ebola monoclonal antibodies.

4 Claims, 4 Drawing Sheets

SEQUENCE LISTING

<160> NUMBER OF SEQ ID NOS: 21

<210> SEQ ID NO 1
<211> LENGTH: 373
<212> TYPE: DNA
<213> ORGANISM: mouse

<400> SEQUENCE: 1

```
tggggcagag cttgtgaagc caggggcctc agtcaagttg tcctgcacag cttctggctt    60
caacattaaa gacacctata tacattgggt gaaacagggg cctgaacagg gcctggagtg   120
gattggaagg attgatcctg cgaatggtaa tactaaaatat gacccgaagt tccagggcaa   180
ggccactatc acagcagaca catcctccaa tacagcctac ctgcagctca gcggcctgac   240
atctgaggac actgccgtct attactgtgc tagggagtcg aggatatcta ctatgcttac   300
gacggggtac tttgactact ggggccaagg caccactctc acagtctcct cagccaaaac   360
aacagcccca tcg                                                       373
```

<210> SEQ ID NO 2
<211> LENGTH: 303
<212> TYPE: DNA
<213> ORGANISM: mouse

<400> SEQUENCE: 2

```
gcaatcatgt ctgcatctcc aggggagaag gtcaccatga cctgcagtgc cagctcaagt    60
gtaagttaca tgtactggta ccagcagaag ccaggatcct cccccagact cctgatttat   120
gacacatcca acctggcttc tggagtccct gttcgcttca gtggcagtgg gtctgggacc   180
tcttactctc tcacaatcag ccgaatggag gctgaagatg ctgccactta ttactgccag   240
cagtggagta gttacccgta cacgttcgga gggggaccaa gctggaaat aaaacgggct   300 gat                                                                  303
```

<210> SEQ ID NO 3
<211> LENGTH: 364
<212> TYPE: DNA
<213> ORGANISM: mouse

<400> SEQUENCE: 3

```
tggaggaggc ttgatgcaac ctggaggatc catgaaactc tcctgtgttg cctcaggatt    60
```

```
cactttcagt aactactgga tgaactgggt ccgccagtct ccagagaagg ggcttgagtg    120
ggttgctgaa attagattga aatctaataa ttatgcaaca cattatgcgg agtctgtgaa    180
agggaggttc accatttcaa gagatgattc caaaaggagt gtctacctgc aaatgaatac    240
cttaagagct gaagacactg gcatttatta ctgtacccgg gggaatggta actacagggc    300
tatggactac tggggtcaag gaacctcagt caccgtctcc tcagccaaaa caacacccca    360
atca                                                                 364

<210> SEQ ID NO 4
<211> LENGTH: 306
<212> TYPE: DNA
<213> ORGANISM: mouse

<400> SEQUENCE: 4
gcctccctat ctgtatctgt gggagaaact gtctccatca catgtcgagc aagtgagaat     60
atttacagta gtttagcatg gtatcagcag aaacagggaa atctcctcag ctcctggtc    120 tattctgcaa caatcttagc agatggtgtg ccatcaaggt tcagtggcag tggatcaggc    180
actcagtatt ccctcaagat caacagcctg cagtctgaag attttgggac ttattactgt    240 caacatttt ggggtactcc gtacacgttc ggaggggga ccaagctgga aataaaacgg    300
gctgat                                                               306

<210> SEQ ID NO 5
<211> LENGTH: 358
<212> TYPE: DNA
<213> ORGANISM: mouse

<400> SEQUENCE: 5
tggacctgag ctggagatgc ctggcgcttc agtgaagata tcctgcaagg cttctggttc     60
ctcattcact ggcttcagta tgaactgggt gaagcagagc aatggaaaga gccttgagtg    120
gattggaaat attgatactt attatggtgg tactacctac aaccagaaat tcaagggcaa    180
ggccacattg actgtggaca atcctccag cacagcctac atgcagctca agagcctgac    240
atctgaggac tctgcagtct attactgtgc aagatcggcc tactacggta gtacttttgc    300
ttactggggc caaggactc tggtcactgt ctctgcagcc aaaacaacag ccccatcg    358

<210> SEQ ID NO 6
<211> LENGTH: 306
<212> TYPE: DNA
<213> ORGANISM: mouse

<400> SEQUENCE: 6
gcctccctat ctgcatctgt gggagaaact gtcaccatca catgtcgagc aagtgagaat     60
atttacagtt atttagcatg gtatcagcag aaacagggaa atctcctca gctcctggtc    120 tataatgcca aaaccttaat agagggtgtg ccatcaaggt tcagtggcag tggatcaggc    180
acacagtttt ctctgaagat caacagcctg cagcctgaag attttgggag ttatttctgt    240
caacatcatt ttggtactcc attcacattc ggctcgggga cagagttgga aataaaacgg    300
gctgat                                                               306

<210> SEQ ID NO 7
<211> LENGTH: 340
<212> TYPE: DNA
<213> ORGANISM: mouse
```

<400> SEQUENCE: 7

```
gggacctggc ctggtgagac cttctcagtc tctgtccctc acctgcactg tcactggcta    60
ctcaatcacc agtgattatg cctggaactg gatccggcag tttccaggaa acaaactgga   120
gtggctgggt tatataacca acactggtag cactggcttc aacccatctc tcaaaagtcg   180
aatctctatc actcgagaca catccaagaa ccagttcttc ctgcagttga tttctgtgac   240
tactgaggac acagccacat atcactgtgc aaggggcctt gcttactggg gccaagggac   300
tctggtcact gtctctgcag ccaaaacaac agccccatcg                         340
```

<210> SEQ ID NO 8
<211> LENGTH: 321
<212> TYPE: DNA
<213> ORGANISM: mouse

<400> SEQUENCE: 8

```
ctcactttgt cggttaccat tggacaacca gcctccatct cttgcaagtc aagtcagagc    60
ctcttagata gtgatggaaa gacatatctg aattggttgt tacagaggcc aggccagtct   120
ccaaagcgcc taatctatct ggtgtctaaa ctggactctg gagtcactga caggttcact   180
ggcagtggat cagggacaga tttcacactg aaaatcagca gagtggaggc tgaggatttg   240
ggagtttatt attgttggca aggtacacac tctccattca cgttcggctc ggggacaaag   300
ttggaaataa aacgggctga t                                             321
```

<210> SEQ ID NO 9
<211> LENGTH: 370
<212> TYPE: DNA
<213> ORGANISM: mouse

<400> SEQUENCE: 9

```
tgggggaggc ttagtgaagc ctggagggtc cctgaaactc tcctgtgcag cctctggatc    60
cgctttcagt agatatgaca tgtcttgggt tcgccagact ccggagaaga ggctggagtg   120
ggtcgcatac attagtcgtg gtggtggttt catctactat ccagacactg tgaagggccg   180
attcaccatc tccagagaca atgccaagaa caccctgtac ctgcaaatga gcagtctgaa   240
gtctgacgac acagccatgt attactgtgc aagacacgtt tactacggta gtagccccct   300
ctatgctatg gactactggg gtcaaggaac ctcagtcacc gtctcctcag ccaaaacaac   360
agccccatcg                                                          370
```

<210> SEQ ID NO 10
<211> LENGTH: 324
<212> TYPE: DNA
<213> ORGANISM: mouse

<400> SEQUENCE: 10

```
tcagcctctt tctccctggg agcctcagca aaactcacgt gcaccttgag tagtcagcac    60
agtacgttca ccattgaatg gtatcagcaa cagccactca agcctcctaa gtatgtgatg   120
gagcttaaga aagatggaag ccacagtaca ggtgatggga ttcctgatcg cttctctgga   180
tccagctctg gtgctgatcg ctaccttagc atttccaaca tccagcctga agatgaagca   240
atatacatct gtggtgtggg tgatacaatt aatgaacaat tgtgtatgt tttcggcggt   300
ggaaccaagg tcactgtcct aggt                                          324
```

<210> SEQ ID NO 11
<211> LENGTH: 358

```
<212> TYPE: DNA
<213> ORGANISM: mouse

<400> SEQUENCE: 11
tggggcagag cttgtgaagc caggggcctc agtcaagttg tcctgcacag cttctggctt      60
caacattaaa gacacctata tgcactgggt gaaggagagg cctgacaagg gcctggagtg     120
gattggaagg attgatccag cgaatggtaa tactaaatgt gactcgaggt ttcagggcaa     180
ggccactata acagcagaca catcctccaa cacagcctac ctgcagctca gcagcctgac     240
atctgaggac actgccgtct attactgtgc tagaaggatc tactttggta agggctttga     300
cttttggggc caaggcacca ctctcacagt ctcctcagcc aaaacaacag ccccatcg      358

<210> SEQ ID NO 12
<211> LENGTH: 324
<212> TYPE: DNA
<213> ORGANISM: mouse

<400> SEQUENCE: 12
tcctcccgta gtgtgtcagc aggagagaag gtcactatga gctgcaagtc cagtcagagt      60
ctgtttaaca gtgagatca aaagaactac ttggcctggt accagcagaa accagggcag      120
cctcctaaac tgttgatcta cggggcatcc actagggaat ctggggtccc tgatcgcttc     180
acaggcagtg gatctggaac cgatttcact cttaccatca gcagtgtgca ggctgaagac     240
ctggcagttt attactgtca gaatgatcaa ttttatcctc ccacgttcgg tgatgggacc     300
aagctggacc tgaaacgggc tgat                                              324

<210> SEQ ID NO 13
<211> LENGTH: 367
<212> TYPE: DNA
<213> ORGANISM: mouse

<400> SEQUENCE: 13 tggaggggggc ttggtacagc ctgggggttc tctgagactc tcctgtgcaa cttctggctt      60
cacctttact gatcactaca tgggctgggt ccgccagcct ccaggaaagg cacttgagtg     120
gttggctttt gttagataca aagctaaggg ttacacaaca gagtacactg catctgtgaa     180
gggtcggttc accatctcca gagataattc ccaaagcatc ctctatcttc aaatgaacac     240
cctgagaact gaggacagtg ccacttatta ctgtgcaaga gatagagggg gttacgtggg     300
agctatggac tactggggtc aaggaacctc agtcaccgtc tcctcagcca aaacgacacc     360
cccatct                                                                 367

<210> SEQ ID NO 14
<211> LENGTH: 321
<212> TYPE: DNA
<213> ORGANISM: mouse

<400> SEQUENCE: 14
ctctccctgc ctgtcagtct tggagatcaa gcctccatct cttgcagatc tagtcagagc      60
cttgtacaca ggaatggaaa cacctatttc cattggtacc tgcagaagcc aggccagtct     120
ccaaaactcc tgatctacaa agtttccaac cgatttctg gggtcccaga caggttcagt      180
ggcagtggat cagggacaga tttcacactc aagatcagca gagtggaggc tgaggatctg     240
ggagtttatt tctgctctca agtacacat gttccgtaca ctttcggagg ggggaccaag     300
ctggaaataa aacgggctga t                                                 321
```

<210> SEQ ID NO 15
<211> LENGTH: 352
<212> TYPE: DNA
<213> ORGANISM: mouse

<400> SEQUENCE: 15

```
tggggcagag cttgtgaggt caggggcctc agtcaagttg tcctgcacat cttctggctt    60
caacattaaa gactactttc tacactgggt gaaacagagg cctgaacagg gcctggagtg   120
gattggatgg attgatcctg agaatggtga tactgaatat gccccgaagt tccaggacaa   180
ggccactatg actgcagaca catcctccaa cacagcctac ctgcacctca gcagcctgac   240
atctgaggac actggcgtct attactgtaa tgcagatggt aactacggga agaactactg   300
gggccaaggc accactctca ccgtctcctc agccaaaaca acagccccat cg           352
```

<210> SEQ ID NO 16
<211> LENGTH: 324
<212> TYPE: DNA
<213> ORGANISM: mouse

<400> SEQUENCE: 16

```
ctctcccctgc ctgtcagtct tggagatcaa gcctccatct cttgcagatc tagtcagagc    60
cttgtacaca gtaatggaaa cacctttta cattggtacc tgcagaagcc aggccagtct    120
ccaaagctcc tgatctacag agtttccaac cgatttctg gggtcccaga caggttcagt    180
ggcagtggat cagggacaga tttcacactc aagatcagca gagtggaggc tgaggatctg    240
ggagtttatt tctgctctca aagtacacat gttcctccgt acacgttcgg aggggggacc    300
aagctggaaa taaaacgggc tgat                                            324
```

<210> SEQ ID NO 17
<211> LENGTH: 15
<212> TYPE: PRT
<213> ORGANISM: mouse

<400> SEQUENCE: 17

Ser Asn Thr Thr Gly Lys Leu Ile Trp Lys Val Asn Pro Glu Ile
1               5                   10                  15

<210> SEQ ID NO 18
<211> LENGTH: 15
<212> TYPE: PRT
<213> ORGANISM: mouse

<400> SEQUENCE: 18

Arg Glu Ala Ile Val Asn Ala Gln Pro Lys Cys Asn Pro Asn Leu
1               5                   10                  15

<210> SEQ ID NO 19
<211> LENGTH: 15
<212> TYPE: PRT
<213> ORGANISM: mouse

<400> SEQUENCE: 19

Arg Glu Ala Ile Val Asn Ala Gln Pro Lys Cys Asn Pro Asn Leu
1               5                   10                  15

<210> SEQ ID NO 20
<211> LENGTH: 15
<212> TYPE: PRT
<213> ORGANISM: mouse

```
<400> SEQUENCE: 20

Asp Pro Gly Thr Asn Thr Thr Thr Glu Asp His Lys Ile Met Ala
1               5                   10                  15

<210> SEQ ID NO 21
<211> LENGTH: 15
<212> TYPE: PRT
<213> ORGANISM: mouse

<400> SEQUENCE: 21

Ala Thr Gln Val Glu Gln His His Arg Arg Thr Asp Asn Asp Ser
1               5                   10                  15
```

MONOCLONAL ANTIBODIES FOR EBOLA AND MARBURG VIRUSES

PRIOR APPLICATION INFORMATION

The instant application is a divisional application of U.S. Ser. No. 12/864,584, filed Oct. 26, 2010, which was a 371 of PCT Application CA2009/000070, filed Jan. 27, 2009, now abandoned, which claims the benefit of U.S. Provisional Patent Application 61/025,491, filed Feb. 1, 2008.

BACKGROUND OF THE INVENTION

Ebola and Marburg viruses are highly pathogenic and virulent viruses causing rapidly fatal haemorrhagic fever in humans.

SUMMARY OF THE INVENTION

According to a first aspect of the invention, there is provided a monoclonal antibody comprising an amino acid sequence deduced from 1H3-light (SEQ ID No. 2); 2G4-light (SEQ ID No. 4); 4G7-light (SEQ ID No. 6); 5D2-light (SEQ ID No. 8); 5E6-light (SEQ ID No. 10); 7C9-light (SEQ ID No. 12); 7G4-light (SEQ ID No. 14), 10C8-light (SEQ ID No. 16), 1H3-heavy (SEQ ID No. 1); 2G4-heavy (SEQ ID No. 3); 4G7-heavy (SEQ ID No. 5); 5D2-heavy (SEQ ID No. 7), 5E6-heavy (SEQ ID No. 9), 7C9-heavy (SEQ ID No. 11), 7G4-heavy (SEQ ID No. 13) and 10C8-heavy (SEQ ID No. 15).

According to a second aspect of the invention, there is provided a method of preparing a chimeric antibody comprising:

providing an expression vector comprising a nucleic acid molecule encoding a constant region domain of a human light chain or heavy chain genetically linked to a nucleic acid encoding a light chain variable region selected from the group consisting of 1H3-light (SEQ ID No. 2); 2G4-light (SEQ ID No. 4); 4G7-light (SEQ ID No. 6); 5D2-light (SEQ ID No. 8); 5E6-light (SEQ ID No. 10); 7C9-light (SEQ ID No. 12); 7G4-light (SEQ ID No. 14) and 10C8-light (SEQ ID No. 16) or a heavy chain variable region selected from the group consisting of 1H3-heavy (SEQ ID No. 1); 2G4-heavy (SEQ ID No. 3); 4G7-heavy (SEQ ID No. 5); 5D2-heavy (SEQ ID No. 7), 5E6-heavy (SEQ ID No. 9), 7C9-heavy (SEQ ID No. 11), 7G4-heavy (SEQ ID No. 13) and 10C8-heavy (SEQ ID No. 15);

expressing the expression vector in a suitable host; and
recovering the chimeric antibody from said host.

According to a third aspect of the invention, there is provided a method of preparing a recombinant antibodies comprising:

providing a nucleotide sequence selected from the group consisting of 1H3-light (SEQ ID No. 2); 2G4-light (SEQ ID No. 4); 4G7-light (SEQ ID No. 6); 5D2-light (SEQ ID No. 8); 5E6-light (SEQ ID No. 10); 7C9-light (SEQ ID No. 12); 7G4-light (SEQ ID No. 14), 10C8-light (SEQ ID No. 16), 1H3-heavy (SEQ ID No. 1); 2G4-heavy (SEQ ID No. 3); 4G7-heavy (SEQ ID No. 5); 5D2-heavy (SEQ ID No. 7), 5E6-heavy (SEQ ID No. 9), 7C9-heavy (SEQ ID No. 11), 7G4-heavy (SEQ ID No. 13) and 10C8-heavy (SEQ ID No. 15);

modifying said nucleic acid sequence such that at least one but fewer than about 30 of the amino acid residues encoded by said nucleic acid sequence has been changed or deleted without disrupting antigen binding of said peptide; and expressing and recovering said modified nucleotide sequence.

BRIEF DESCRIPTION OF THE DRAWINGS

FIG. 2. Weight changes of GPA-Ebola infected guinea pigs treated with MAbs. Weight changes of virus-infected guinea pigs treated with cocktail of MAbs. Guinea pigs were intraperitoneally treated with either 5D2, 5E6, 7C9, 7G4 or 10C8 (3 mg/treatment) on day 1 and 4G7+1H3+2G4 [(2 mg+1 mg+1 mg)/treatment] on day 2. Control guinea pig were given equal volume of PBS. The results are shown as the means and standard deviations of 6 guinea pigs.

DESCRIPTION OF THE PREFERRED EMBODIMENTS

Unless defined otherwise, all technical and scientific terms used herein have the same meaning as commonly understood by one of ordinary skill in the art to which the invention belongs. Although any methods and materials similar or equivalent to those described herein can be used in the practice or testing of the present invention, the preferred methods and materials are now described. All publications mentioned hereunder are incorporated herein by reference.

DEFINITIONS

As used herein, "neutralizing antibody" refers to an antibody, for example, a monoclonal antibody, capable of disrupting a formed viral particle or inhibiting formation of a viral particle or prevention of binding to or infection of mammalian cells by a viral particle.

As used herein, "diagnostic antibody" or "detection antibody" or "detecting antibody" refers to an antibody, for example, a monoclonal antibody, capable of detecting the presence of an antigenic target within a sample. As will be appreciated by one of skill in the art, such diagnostic antibodies preferably have high specificity for their antigenic target.

As used herein, "humanized antibodies" refer to antibodies with reduced immunogenicity in humans.

As used herein, "chimeric antibodies" refer to antibodies with reduced immunogenicity in humans built by genetically linking a non-human Variable region to human constant domains.

Described herein are a number of Ebola and Marburg monoclonal antibodies. Specifically, antigens were developed using a live replicating vector vesicular stomatitis virus described in PCT Application PCT/CA03/001125.

The VSV based vaccine delivery system was used to develop monoclonal antibodies in mice.

Specifically, described herein are monoclonal antibodies 1H3, 2G4, 4G7, 5D2, 5E6, 7C9, 7G4 and 10C8. As discussed below, 1H3 comprises 1H3-heavy chain (SEQ ID No. 1) and 1H3-light chain (SEQ ID No. 2); 2G4 comprises 2G4-heavy chain (SEQ ID No. 3) and 2G4-light chain (SEQ ID No. 4); 4G7 comprises 4G7-heavy chain (SEQ ID No. 5) and 4G7-light chain (SEQ ID No. 6); 5D2 comprises 5D2-heavy chain (SEQ ID No. 7) and 5D2-light chain (SEQ ID No. 8); 5E6 comprises 5E6-heavy chain (SEQ ID No. 9) and 5E6-light chain (SEQ ID No. 10); 7C9 comprises 7C9-heavy chain (SEQ ID No. 11) and 7C9-light chain (SEQ ID No. 12); 7G4 comprises 7G4-heavy chain (SEQ ID No. 13) and 7G4-light chain (SEQ ID No. 14); and 10C8 comprises 10C8-light chain (SEQ ID No. 16) and 10C8-heavy chain (SEQ ID No. 15).

These antibodies also appear to have high affinity and avidity to Ebola glycoproteins, which means that they could be used as highly sensitive diagnostic tools.

Figure 1:
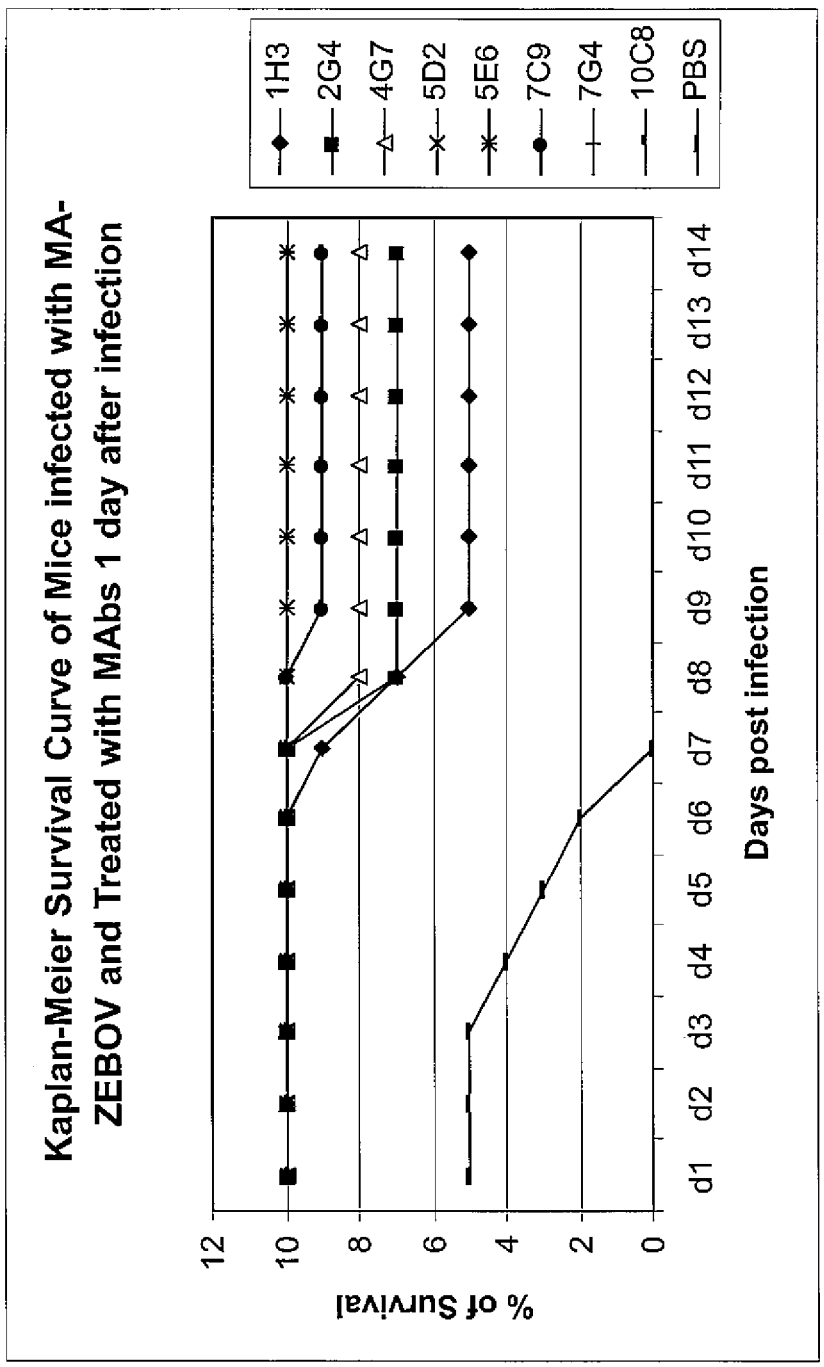
FIG. 1. Kaplan-Meier survival curve of mice infected with MA-ZEBOV and treated with MAbs 1 day after infection. Survival curve of MA-Ebola virus-infected mice treated with 100 µg of MAbs. Mice were intraperitoneally treated with 100 µg of each MAb on day 1. Control mice were given equal volumes of PBS.

For example, as shown in FIG. 1, mice infected with MA-ZEBOV and subsequently treated with the monoclonal antibodies described above showed increased survival compared to mice treated with PBS. Results are summarized in Tables 1 and 2.

Figure 2:
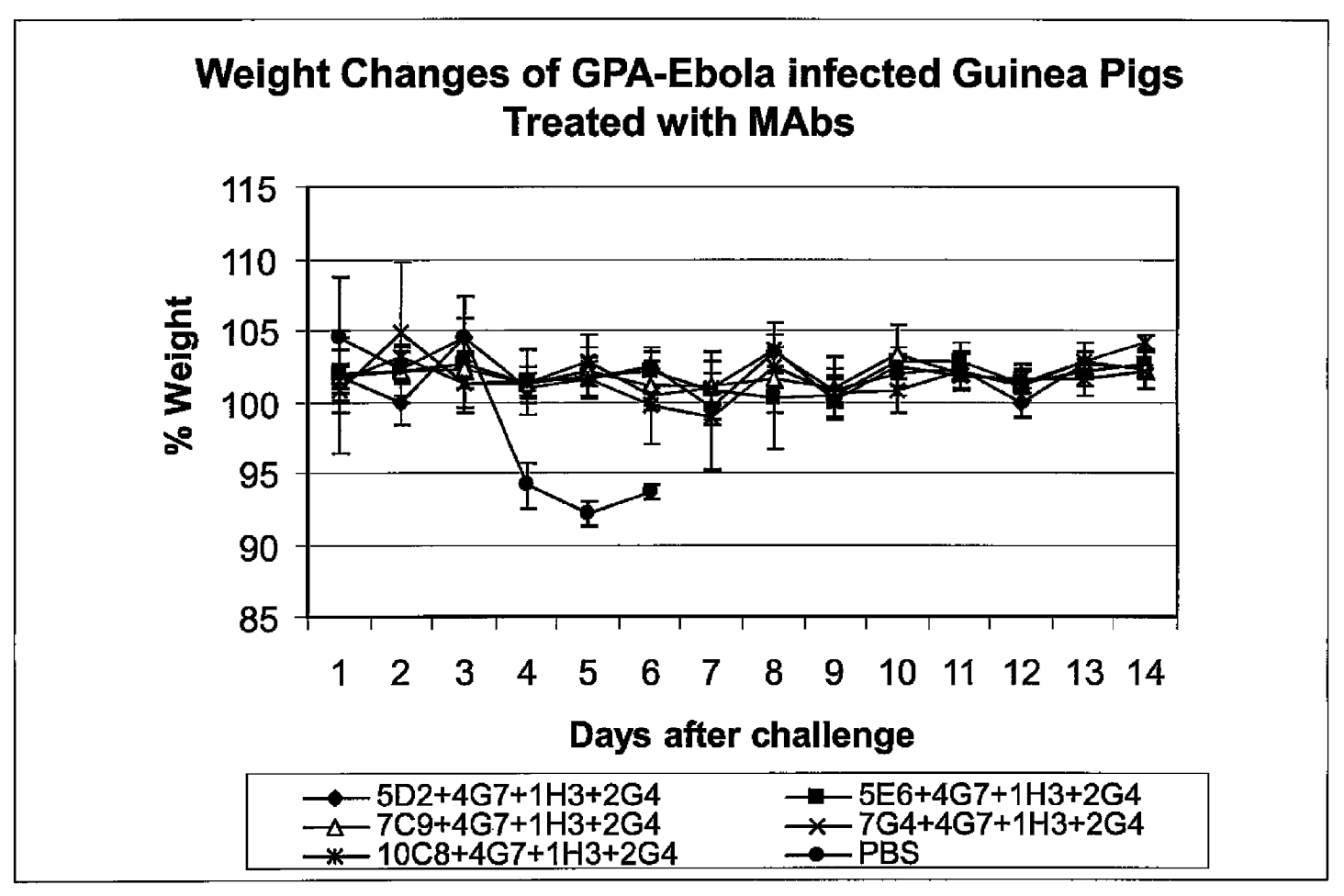
Figure 3:
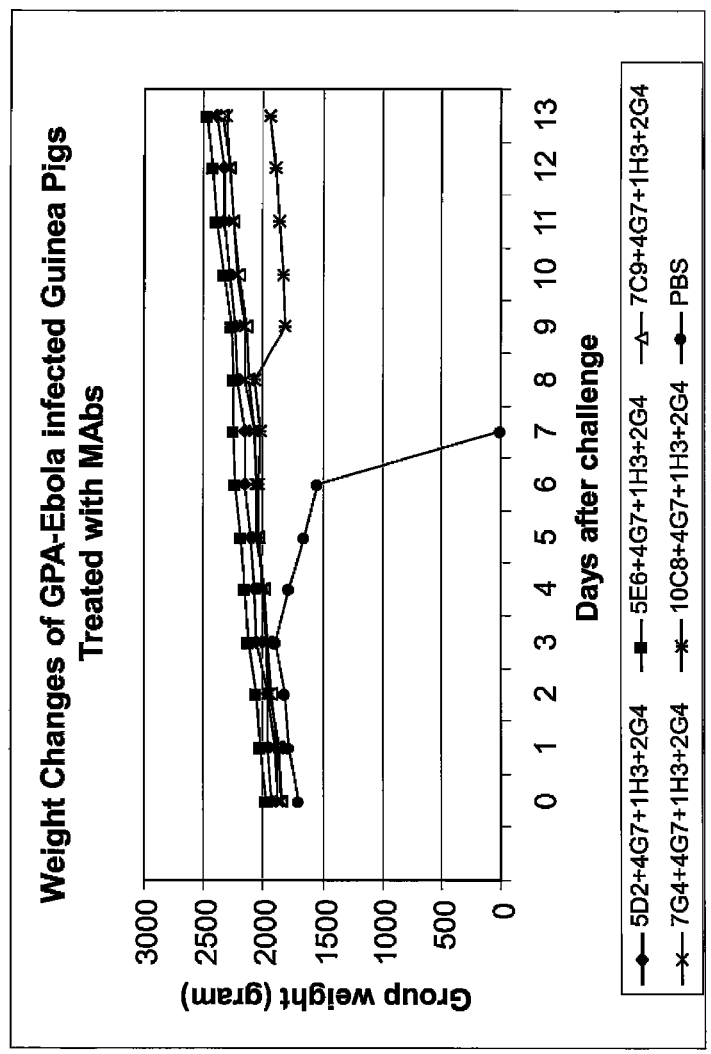
FIG. 3. Weight changes of GPA-Ebola infected guinea pigs treated with MAbs. Weight changes of virus-infected guinea pigs treated with cocktail of MAbs. Guinea pigs were intraperitoneally treated with either 5D2, 5E6, 7C9, 7G4 or 10C8 (3 mg/treatment) on day 1 and 4G7+1 H3+2G4 [(2 mg+1 mg+1 mg)/treatment] on day 2. Control guinea pig were given equal volume of PBS. The results are shown as the group weight of 6 guinea pigs.
Figure 4:
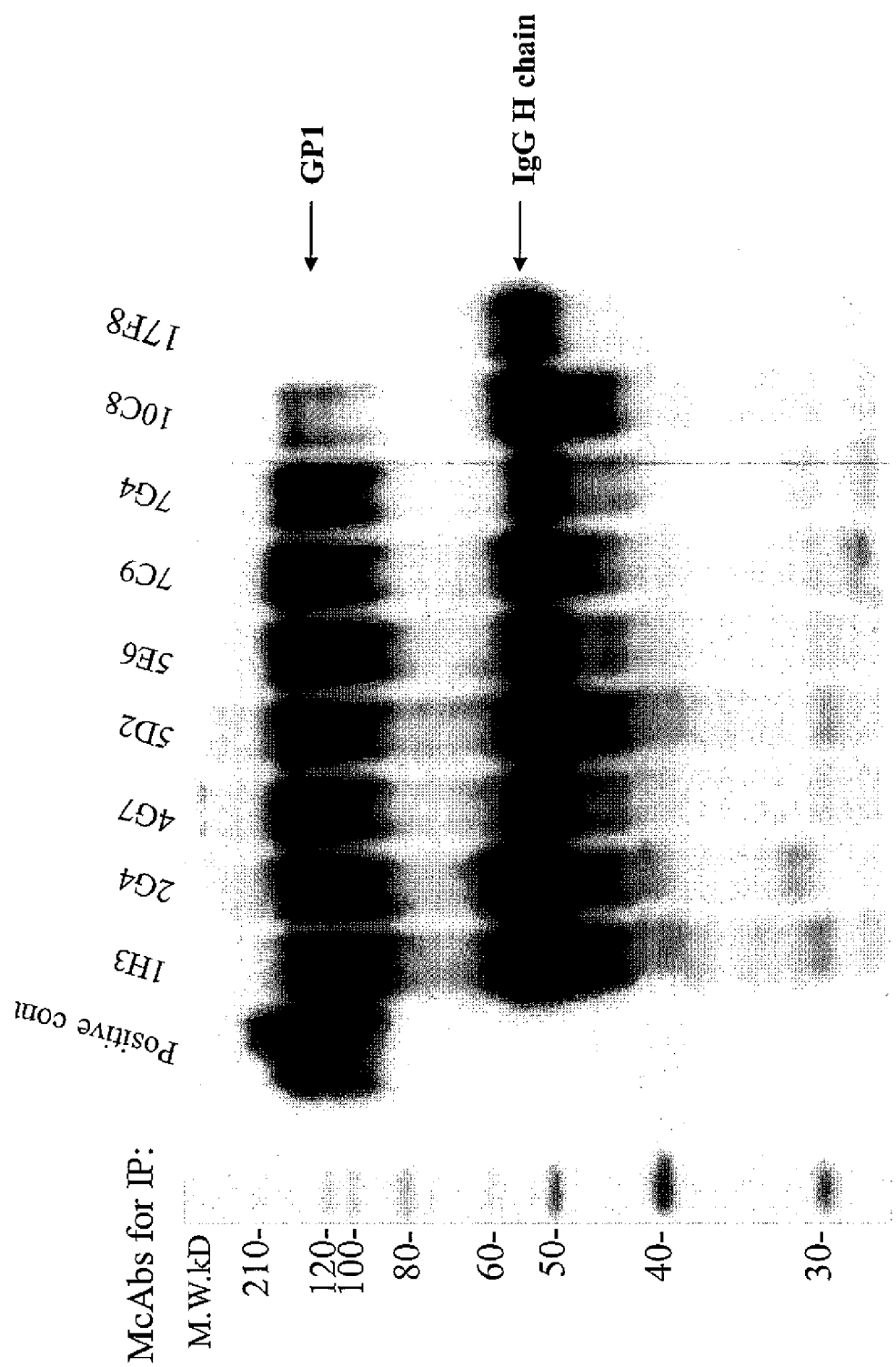
FIG. 4. Immunoprecipitation. 293T cells were transfected with pCAGGS-ZEbovGP1,2 by using Fugene 6. After 48 hrs, cells were collected and washed 2× with cold PBS before being lysed with 2× RIPA buffer. After clarifying the cell lysate, 100 µg protein was added to each McAb (5 µg) coupled protein A+G beads. The IP samples were run 10% SDS-PAGE and transferred to Hybond-P membrane. The blot was probed with mouse ant-EBOV-GP1.

FIGS. 2 and 3 show weight changes in guinea pigs treated with the monoclonal antibodies or mixtures thereof post infection. As can be seen, guinea pigs treated with the monoclonal antibodies showed consistent weight while those treated with PBS showed significant weight loss. Results are summarized in Table 3.

The nucleotide sequences of the heavy and light chains of 1H3, 2G4, 4G7, 5D2, 5E6, 7C9, 7G4 and 10C8 follow. As will be appreciated by one of skill in the art, the amino acid sequences of these antibodies can easily be deduced from the nucleotide sequences. Accordingly, in some embodiments, the invention is directed to amino acid sequences deduced from 1H3-light (SEQ ID No. 2); 2G4-light (SEQ ID No. 4); 4G7-light (SEQ ID No. 6); 5D2-light (SEQ ID No. 8); 5E6-light (SEQ ID No. 10); 7C9-light (SEQ ID No. 12); 7G4-light (SEQ ID No. 14), 10C8-light (SEQ ID No. 16), 1H3-heavy (SEQ ID No. 1); 2G4-heavy (SEQ ID No. 3); 4G7-heavy (SEQ ID No. 5); 5D2-heavy (SEQ ID No. 7), 5E6-heavy (SEQ ID No. 9), 7C9-heavy (SEQ ID No. 11), 7G4-heavy (SEQ ID No. 13) and 10C8-heavy (SEQ ID No. 15).

mAb 1H3 heavy chain sequence: 373 bp (SEQ ID No. 1)
TGGGGCAGAGCTTGTGAAGCCAGGGGCCTCAGTCAAGTTGTCCTGCACAG

CTTCTGGCTTCAACATTAAAGACACCTATATACATTGGGTGAAACAGGGG

CCTGAACAGGGCCTGGAGTGGATTGGAAGGATTGATCCTGCGAATGGTAA

TACTAAATATGACCCGAAGTTCCAGGGCAAGGCCACTATCACAGCAGACA

CATCCTCCAATACAGCCTACCTGCAGCTCAGCGGCCTGACATCTGAGGAC

ACTGCCGTCTATTACTGTGCTAGGGAGTCGAGGATATCTACTATGCTTAC

GACGGGGTACTTTGACTACTGGGGCCAAGGCACCACTCTCACAGTCTCCT

CAGCCAAAACAACAGCCCCATCG mAb 1H3 light chain sequence: 303 bp (SEQ ID No. 2)
GCAATCATGTCTGCATCTCCAGGGGAGAAGGTCACCATGACCTGCAGTGC

CAGCTCAAGTGTAAGTTACATGTACTGGTACCAGCAGAAGCCAGGATCCT

CCCCCAGACTCCTGATTTATGACACATCCAACCTGGCTTCTGGAGTCCCT

GTTCGCTTCAGTGGCAGTGGGTCTGGGACCTCTTACTCTCTCACAATCAG

CCGAATGGAGGCTGAAGATGCTGCCACTTATTACTGCCAGCAGTGGAGTA

GTTACCCGTACACGTTCGGAGGGGGGACCAAGCTGGAAATAAAACGGGCT

GAT mAb 2G4 heavy chain sequence: 364 bp (SEQ ID No. 3)
TGGAGGAGGCTTGATGCAACCTGGAGGATCCATGAAACTCTCCTGTGTTG

CCTCAGGATTCACTTTCAGTAACTACTGGATGAACTGGGTCCGCCAGTCT

CCAGAGAAGGGGCTTGAGTGGGTTGCTGAAATTAGATTGAAATCTAATAA

TTATGCAACACATTATGCGGAGTCTGTGAAAGGGAGGTTCACCATTTCAA

GAGATGATTCCAAAAGGAGTGTCTACCTGCAAATGAATACCTTAAGAGCT

GAAGACACTGGCATTTATTACTGTACCCGGGGGAATGGTAACTACAGGGC

TATGGACTACTGGGGTCAAGGAACCTCAGTCACCGTCTCCTCAGCCAAAA

CAACACCCCCATCA mAb 2G4 light chain sequence: 306 bp (SEQ ID No. 4)
GCCTCCCTATCTGTATCTGTGGGAGAAACTGTCTCCATCACATGTCGAGC

AAGTGAGAATATTTACAGTAGTTTAGCATGGTATCAGCAGAAACAGGGAA

AATCTCCTCAGCTCCTGGTCTATTCTGCAACAATCTTAGCAGATGGTGTG

CCATCAAGGTTCAGTGGCAGTGGATCAGGCACTCAGTATTCCCTCAAGAT

CAACAGCCTGCAGTCTGAAGATTTTGGGACTTATTACTGTCAACATTTTT

GGGGTACTCCGTACACGTTCGGAGGGGGGACCAAGCTGGAAATAAAACGG

GCTGAT mAb 4G7 heavy chain sequence: 358 bp (SEQ ID No. 5)
TGGACCTGAGCTGGAGATGCCTGGCGCTTCAGTGAAGATATCCTGCAAGG

CTTCTGGTTCCTCATTCACTGGCTTCAGTATGAACTGGGTGAAGCAGAGC

AATGGAAAGAGCCTTGAGTGGATTGGAAATATTGATACTTATTATGGTGG

TACTACCTACAACCAGAAATTCAAGGGCAAGGCCACATTGACTGTGGACA

AATCCTCCAGCACAGCCTACATGCAGCTCAAGAGCCTGACATCTGAGGAC

TCTGCAGTCTATTACTGTGCAAGATCGGCCTACTACGGTAGTACTTTTGC

TTACTGGGGCCAAGGGACTCTGGTCACTGTCTCTGCAGCCAAAACAACAG

CCCCATCG mAb 4G7 light chain sequence: 306 bp (SEQ ID No. 6)
GCCTCCCTATCTGCATCTGTGGGAGAAACTGTCACCATCACATGTCGAGC

AAGTGAGAATATTTACAGTTATTTAGCATGGTATCAGCAGAAACAGGGAA

AATCTCCTCAGCTCCTGGTCTATAATGCCAAAACCTTAATAGAGGGTGTG

CCATCAAGGTTCAGTGGCAGTGGATCAGGCACACAGTTTTCTCTGAAGAT

CAACAGCCTGCAGCCTGAAGATTTTGGGAGTTATTTCTGTCAACATCATT

TTGGTACTCCATTCACATTCGGCTCGGGGACAGAGTTGGAAATAAAACGG

GCTGAT mAb 5D2 heavy chain sequence: 340 bp (SEQ ID No. 7)
GGGACCTGGCCTGGTGAGACCTTCTCAGTCTCTGTCCCTCACCTGCACTG

TCACTGGCTACTCAATCACCAGTGATTATGCCTGGAACTGGATCCGGCAG

TTTCCAGGAAACAAACTGGAGTGGCTGGGCTATATAACCAACACTGGTAG

CACTGGCTTCAACCCATCTCTCAAAAGTCGAATCTCTATCACTCGAGACA

CATCCAAGAACCAGTTCTTCCTGCAGTTGATTTCTGTGACTACTGAGGAG

ACAGCCACATATCACTGTGCAAGGGGCCTTGCTTACTGGGGCCAAGGGAC

TCTGGTCACTGTCTCTGCAGCCAAAACAACAGCCCCATCG mAb 5D2 light chain sequence: 321 bp (SEQ ID No. 8)
CTCACTTTGTCGGTTACCATTGGACAACCAGCCTCCATCTCTTGCAAGTC

AAGTCAGAGCCTCTTAGATAGTGATGGAAAGACATATCTGAATTGGTTGT

TACAGAGGCCAGGCCAGTCTCCAAAGCGCCTAATCTATCTGGTGTCTAAA

CTGGACTCTGGAGTCACTGACAGGTTCACTGGCAGTGGATCAGGGACAGA

TTTCACACTGAAAATCAGCAGAGTGGAGGCTGAGGATTTGGGAGTTTATT

ATTGTTGGCAAGGTACACACTCTCCATTCACGTTCGGCTCGGGGACAAAG

TTGGAAATAAAACGGGCTGAT mAb 5E6 heavy chain sequence: 370 bp (SEQ ID No. 9)
TGGGGGAGGCTTAGTGAAGCCTGGAGGGTCCCTGAAACTCTCCTGTGCAG

CCTCTGGATCCGCTTTCAGTAGATATGACATGTCTTGGGTTCGCCAGACT

CCGGAGAAGAGGCTGGAGTGGGTCGCATACATTAGTCGTGGTGGTGGTTT

CATCTACTATCCAGACACTGTGAAGGGCCGATTCACCATCTCCAGAGACA

ATGCCAAGAACACCCTGTACCTGCAAATGAGCAGTCTGAAGTCTGACGAC

ACAGCCATGTATTACTGTCAAGACACGTTTACTACGGTAGTAGCCCCCT

CTATGCTATGGACTACTGGGGTCAAGGAACCTCAGTCACCGTCTCCTCAG

CCAAAACAACAGCCCCATCG mAb 5E6 light chain sequence: 324 bp (SEQ ID No. 10)
TCAGCCTCTTTCTCCCTGGGAGCCTCAGCAAAACTCACGTGCACCTTGAG

TAGTCAGCACAGTACGTTCACCATTGAATGGTATCAGCAACAGCCACTCA

AGCCTCCTAAGTATGTGATGGAGCTTAAGAAAGATGGAAGCCACAGTACA

GGTGATGGGATTCCTGATCGCTTCTCTGGATCCAGCTCTGGTGCTGATCG

CTACCTTAGCATTTCCAACATCCAGCCTGAAGATGAAGCAATATACATCT

GTGGTGTGGGTGATACAATTAATGAACAATTTGTGTATGTTTTCGGCGGT

GGAACCAAGGTCACTGTCCTAGGT mAb 7C9 heavy chain sequence: 358 bp (SEQ ID No. 11)
TGGGGCAGAGCTTGTGAAGCCAGGGGCCTCAGTCAAGTTGTCCTGCACAG

CTTCTGGCTTCAACATTAAAGACACCTATATGCACTGGGTGAAGGAGAGG

CCTGACAAGGGCCTGGAGTGGATTGGAAGGATTGATCCAGCGAATGGTAA

TACTAAATGTGACTCGAGGTTTCAGGGCAAGGCCACTATAACAGCAGACA

CATCCTCCAACACAGCCTACCTGCAGCTCAGCAGCCTGACATCTGAGGAC

ACTGCCGTCTATTACTGTGCTAGAAGGATCTACTTTGGTAAGGGCTTTGA

CTTTTGGGGCCAAGGCACCACTCTCACAGTCTCCTCAGCCAAAACAACAG

CCCCATCG mAb 7C9 light chain sequence: 324 bp (SEQ ID No. 12)
TCCTCCCTGAGTGTGTCAGCAGGAGAGAAGGTCACTATGAGCTGCAAGTC

CAGTCAGAGTCTGTTTAACAGTGGAGATCAAAAGAACTACTTGGCCTGGT

ACCAGCAGAAACCAGGGCAGCCTCCTAAACTGTTGATCTACGGGGCATCC

ACTAGGGAATCTGGGGTCCCTGATCGCTTCACAGGCAGTGGATCTGGAAC

CGATTTCACTCTTACCATCAGCAGTGTGCAGGCTGAAGACCTGGCAGTTT

ATTACTGTCAGAATGATCAATTTTATCCTCCCACGTTCGGTGATGGGACC

AAGCTGGACCTGAAACGGGCTGAT mAb 7G4 heavy chain sequence: 367 bp (SEQ ID No. 13)
TGGAGGGGCTTGGTACAGCCTGGGGGTTCTCTGAGACTCTCCTGTGCAA

CTTCTGGCTTCACCTTTACTGATCACTACATGGGCTGGGTCCGCCAGCCT

CCAGGAAAGGCACTTGAGTGGTTGGCTTTTGTTAGATACAAAGCTAAGGG

TTACACAACAGAGTACACTGCATCTGTGAAGGGTCGGTTCACCATCTCCA

GAGATAATTCCCAAAGCATCCTCTATCTTCAAATGAACACCCTGAGAACT

GAGGACAGTGCCACTTATTACTGTGCAAGAGATAGGGGGGTTACGTGGG

AGCTATGGACTACTGGGGTCAAGGAACCTCAGTCACCGTCTCCTCAGCCA

AAACGACACCCCCATCT mAb 7G4 light chain sequence: 321 bp (SEQ ID No. 14)
CTCTCCCTGCCTGTCAGTCTTGGAGATCAAGCCTCCATCTCTTGCAGATC

TAGTCAGAGCCTTGTACACAGGAATGGAAACACCTATTTCCATTGGTACC

TGCAGAAGCCAGGCCAGTCTCCAAAACTCCTGATCTACAAAGTTTCCAAC

CGATTTTCTGGGGTCCCAGACAGGTTCAGTGGCAGTGGATCAGGGACAGA

TTTCACACTCAAGATCAGCAGAGTGGAGGCTGAGGATCTGGGAGTTTATT

TCTGCTCTCAAAGTACACATGTTCCGTACACTTTCGGAGGGGGACCAAG

CTGGAAATAAAACGGGCTGAT mAb 10C8 heavy chain sequence: 352 bp (SEQ ID No. 15)
TGGGGCAGAGCTTGTGAGGTCAGGGGCCTCAGTCAAGTTGTCCTGCACAT

CTTCTGGCTTCAACATTAAAGACTACTTTCTACACTGGGTGAAACAGAGG

CCTGAACAGGGCCTGGAGTGGATTGGATGGATTGATCCTGAGAATGGTGA

TACTGAATATGCCCCGAAGTTCCAGGACAAGGCCACTATGACTGCAGACA

CATCCTCCAACACAGCCTACCTGCACCTCAGCAGCCTGACATCTGAGGAC

ACTGGCGTCTATTACTGTAATGCAGATGGTAACTACGGGAAGAACTACTG

GGGCCAAGGCACCACTCTCACCGTCTCCTCAGCCAAAACAACAGCCCCAT

CG mAb 10C8 light chain sequence: 324 bp (SEQ ID No. 16)
CTCTCCCTGCCTGTCAGTCTTGGAGATCAAGCCTCCATCTCTTGCAGATC

TAGTCAGAGCCTTGTACACAGTAATGGAAACACCTTTTTACATTGGTACC

TGGAGAAGCCAGGCCAGTCTCCAAAGCTCCTGATCTACAGAGTTTCCAAC

CGATTTTCTGGGGTCCCAGACAGGTTCAGTGGCAGTGGATCAGGGACAGA

TTTCACACTCAAGATCAGCAGAGTGGAGGCTGAGGATCTGGGAGTTTATT

TCTGCTCTCAAAGTACACATGTTCCTCCGTACACGTTCGGAGGGGGGACC

AAGCTGGAAATAAAACGGGCTGAT

In another embodiment of the invention, one or more of the nucleic acid sequences described above encoding the antibody are subjected to humanization techniques or converted into chimeric human molecules for generating a variant antibody which has reduced immunogenicity in humans. Humanization techniques are well known in the art—see for example U.S. Pat. No. 6,309,636 and U.S. Pat. No. 6,407,213 which are incorporated herein by reference specifically for their disclosure on humanization techniques. Chimerics are also well known, see for example U.S. Pat. No. 6,461,824, U.S. Pat. No. 6,204,023, U.S. Pat. No. 6,020,153 and U.S. Pat. No. 6,120,767 which are similarly incorporated herein by reference.

In one embodiment of the invention, chimeric antibodies are prepared by preparing an expression vector which comprises a nucleic acid encoding a constant region domain of a human light or heavy chain genetically linked to a nucleic acid encoding a light chain variable region selected from the group consisting of 1H3-light (SEQ ID No. 2); 2G4-light (SEQ ID No. 4); 4G7-light (SEQ ID No. 6); 5D2-light (SEQ ID No. 8); 5E6-light (SEQ ID No. 10); 7C9-light (SEQ ID No. 12); 7G4-light (SEQ ID No. 14) and 10C8-light (SEQ ID No. 16) or a heavy chain variable region selected from the group consisting of 1H3-heavy (SEQ ID No. 1); 2G4-heavy (SEQ ID No. 3); 4G7-heavy (SEQ ID No. 5); 5D2-heavy (SEQ ID No. 7), 5E6-heavy (SEQ ID No. 9), 7C9-heavy (SEQ ID No. 11), 7G4-heavy (SEQ ID No. 13) and 10C8-heavy (SEQ ID No. 15). It is of note that all of these sequences are described above.

In another embodiment of the invention, there are provided recombinant antibodies comprising at least one modified variable region, said region selected from the group consisting of 1H3-light (SEQ ID No. 2); 2G4-light (SEQ ID No. 4); 4G7-light (SEQ ID No. 6); 5D2-light (SEQ ID No. 8); 5E6-light (SEQ ID No. 10); 7C9-light (SEQ ID No. 12); 7G4-light (SEQ ID No. 14), 10C8-light (SEQ ID No. 16), 1H3-heavy (SEQ ID No. 1); 2G4-heavy (SEQ ID No. 3); 4G7-heavy (SEQ ID No. 5); 5D2-heavy (SEQ ID No. 7); 5E6-heavy (SEQ ID No. 9), 7C9-heavy (SEQ ID No. 11), 7G4-heavy (SEQ ID No. 13) and 10C8-heavy (SEQ ID No. 15), in which at least one but fewer than about 30 of the amino acid residues of said variable region has been changed or deleted without disrupting antigen binding. It is of note that all of these sequences are described above.

In yet other embodiments, immunoreactive fragments of any of the above-described monoclonal antibodies, chimeric antibodies or humanized antibodies are prepared using means known in the art, for example, by preparing nested deletions using enzymatic degradation or convenient restriction enzymes.

It is of note that in all embodiments describing preparation of humanized antibodies, chimeric antibodies or immunoreactive fragments of monoclonal antibodies, these antibodies are screened to ensure that antigen binding has not been disrupted. This may be accomplished by any of a variety of means known in the art, but one convenient method would involve use of a phage display library. As will be appreciated by one of skill in the art, as used herein, 'immunoreactive fragment' refers in this context to an antibody fragment reduced in length compared to the wild-type or parent antibody which retains an acceptable degree or percentage of binding activity to the target antigen. As will be appreciated by one of skill in the art, what is an acceptable degree will depend on the intended use.

It is of note that as discussed herein, any of the above-described antibody or humanized variant thereof may be formulated into a pharmaceutical treatment for providing passive immunity for individuals suspected of or at risk of developing hemorrhagic fever comprising a therapeutically effective amount of said antibody. The pharmaceutical preparation may include a suitable excipient or carrier. See, for example, Remington: The Science and Practice of Pharmacy, 1995, Gennaro ed. As will be apparent to one knowledgeable in the art, the total dosage will vary according to the weight, health and circumstances of the individual as well as the efficacy of the antibody.

While the preferred embodiments of the invention have been described above, it will be recognized and understood that various modifications may be made therein, and the appended claims are intended to cover all such modifications which may fall within the spirit and scope of the invention.

TABLE 1

Dose-dependent protective efficacy of McAbs in mice

| Treatment[a] | Dose (μg/treatment) | Meantime to death[b] | No. of survivors/total |
|---|---|---|---|
| McAb 4G7 | 100 | 7.00 (n = 1) | 5/6 |
| | 50 | 7.00 (n = 1) | 5/6 |
| | 25 | 6.00 (n = 3) | 3/6 |
| | 12.5 | 6.80 (n = 5) | 1/6 |
| | 6.25 | 8.20 (n = 5) | 2/6 |
| McAb 5D2 | 100 | N/A[c] | 6/6 |
| | 50 | N/A[c] | 6/6 |
| | 25 | N/A[c] | 6/6 |
| | 12.5 | N/A[c] | 6/6 |
| | 6.25 | 7.50 (n = 2) | 4/6 |
| McAb 5E6 | 100 | N/A[c] | 6/6 |
| | 50 | N/A[c] | 6/6 |
| | 25 | N/A[c] | 6/6 |
| | 12.5 | 6.50 (n = 2) | 4/6 |
| | 6.25 | 6.67 (n = 3) | 3/6 |
| McAb 7C9 | 100 | N/A[c] | 6/6 |
| | 50 | N/A[c] | 6/6 |
| | 25 | 7.00 (n = 1) | 5/6 |
| | 12.5 | 7.00 (n = 1) | 5/6 |
| | 6.25 | 6.50 (n = 4) | 2/6 |
| McAb 7G4 | 100 | N/A[c] | 6/6 |
| | 50 | 7.50 (n = 1) | 4/6 |
| | 25 | 7.00 (n = 1) | 5/6 |
| | 12.5 | 7.60 (n = 5) | 1/6 |
| | 6.25 | 6.60 (n = 5) | 1/6 |
| McAb 10C8 | 100 | 7.00 (n = 1) | 5/6 |
| | 50 | 7.00 (n = 1) | 5/6 |
| | 25 | 7.50 (n = 4) | 2/6 |
| | 12.5 | 7.00 (n = 5) | 1/6 |
| | 6.25 | 6.40 (n = 5) | 1/6 |
| PBS | | 5.80 (n = 5) | 0/5 |

[a]Mice were intraperitoneally treated with antibodies 1 day after challenge with 1000 LD50 of the mouse-adapted Ebola virus.
[b]Data for animals that died (numbers of animals are shown in parentheses).
[c]N/A: not applicable.

TABLE 2

Time dependency of the protective efficacy of MAbs in mice

| MAbs | Day of treatment[a] | Mean time to death[b] | No. of survivors/total |
|---|---|---|---|
| 1H3 | −4 | 6.70 ± 0.61 (n = 10) | 0/10 |
| 100 μg | −1 | 6.60 ± 0.61 (n = 10) | 0/15 |
| | +1 | 8.10 ± 0.74 (n = 9) | 6/15 |
| | +2 | 6.60 ± 0.80 (n = 5) | 5/10 |
| | +3 | 6.40 ± 0.97 (n = 10) | 0/10 |
| 2G4 | −4 | 7.40 ± 0.63 (n = 10) | 0/10 |
| 100 μg | −1 | 7.86 ± 0.74 (n = 14) | 1/15 |
| | +1 | 8.00 (n = 6) | 9/15 |
| | +2 | 7.30 ± 0.47 (n = 3) | 7/10 |
| | +3 | 5.70 ± 1.13 (n = 10) | 0/10 |
| 4G7 | −4 | 7.42 ± 0.46 (n = 7) | 3/10 |
| 100 μg | −1 | 7.08 ± 0.74 (n = 14) | 1/15 |
| | +1 | 8.25 ± 0.43 (n = 4) | 11/15 |
| | +2 | n/a[c] | 10/10 |
| | +3 | 5.67 ± 1.34 (n = 9) | 1/10 |
| 5D2 | −4 | 7.00 (n = 1) | 9/10 |
| 100 μg | −1 | 8.00 ± 1.00 (n = 2) | 13/15 |
| | +1 | n/a | 15/15 |
| | +2 | 7.00 (n = 4) | 6/10 |
| | +3 | 6.30 ± 1.05 (n = 10) | 0/10 |
| 5E6 | −4 | 7.00 (n = 2) | 8/10 |
| 100 μg | −1 | 8.25 ± 0.43 (n = 4) | 11/15 |
| | +1 | 7.00 (n = 1) | 14/15 |
| | +2 | 6.00 (n = 1) | 9/10 |
| | +3 | 5.80 ± 1.03 (n = 10) | 0/10 |
| 7C9 | −4 | 7.00 (n = 1) | 9/10 |
| 100 μg | −1 | 7.75 ± 0.43 (n = 4) | 11/15 |
| | +1 | 8.00 ± 0.82 (n = 3) | 12/15 |
| | +2 | 7.00 (n = 1) | 9/10 |
| | +3 | 6.10 ± 0.67 (n = 10) | 0/10 |
| 7G4 | −4 | 8.20 ± 0.71 (n = 10) | 0/10 |
| 100 μg | −1 | 8.07 ± 0.59 (n = 14) | 1/15 |
| | +1 | n/a | 15/15 |
| | +2 | 7.10 ± 0.57 (n = 9) | 1/10 |
| | +3 | 6.70 ± 0.44 (n = 10) | 0/10 |
| 10C8 | −4 | 7.83 ± 0.64 (n = 6) | 4/10 |
| 100 μg | −1 | 7.64 ± 1.17 (n = 14) | 1/15 |
| | +1 | 8.50 ± 0.50 (n = 2) | 13/15 |
| | +2 | 6.83 ± 0.37 (n = 6) | 4/10 |
| | +3 | 6.30 ± 1.13 (n = 10) | 0/10 |
| 17F8[d] | −4 | 6.00 ± 1.10 (n = 9) | 1/10 |
| 100 μg | −1 | 6.13 ± 0.88 (n = 15) | 0/15 |
| | +1 | 7.21 ± 0.86 (n = 14) | 1/15 |
| | +2 | 6.10 ± 0.83 (n = 10) | 0/10 |
| | +3 | 6.00 ± 1.13 (n = 10) | 0/10 |
| PBS | −4 | 5.40 ± 1.43 (n = 10) | 0/10 |
| | −1 | 6.60 ± 0.80 (n = 5) | 0/5 |
| | +3 | 5.00 ± 0.60 (n = 10) | 0/10 |

[a]Mice were intraperitoneally treated with each MAb at indicated time before or after challenge with 1000 LD50 of the mouse-adapted Ebola virus.
[b]Data for animals that died (numbers of animals are shown in parentheses).
[c]N/A: not applicable.
[d]Control Mab: anti-MAR GP.

TABLE 3

Protective efficacy of MAbs in guinea pigs

| Treatment | Day of treatment[a] | Meantime to death[b] | No. of survival/Tatal[c] |
|---|---|---|---|
| Cocktail of 5D2(3 mg) + 4G7(2 mg) + 1H3(1 mg) + 2G4(1 mg) | 1, 2 | N/A[d] | 6/6 |
| Cocktail of 5E6(3 mg) + 4G7(2 mg) + 1H3(1 mg) + 2G4(1 mg) | 1, 2 | N/A | 6/6 |
| Cocktail of 7C9(3 mg) + 4G7(2 mg) + 1H3(1 mg) + 2G4(1 mg) | 1, 2 | N/A | 6/6 |
| Cocktail of 7G4(3 mg) + 4G7(2 mg) + 1H3(1 mg) + 2G4(1 mg) | 1, 2 | N/A | 6/6 |
| Cocktail of 10C8(3 mg) + 4G7(2 mg) + 1H3(1 mg) + 2G4(1 mg) | 1, 2 | 9.00 (n = 1) | 5/6 |
| Cocktail of PBS + PBS | 1, 2 | 7.00 (n = 6) | 0/6 |

[a]Guinea pigs were intraperiotoneally treated with the MAbs as showed dose in the table on the indicated days after challenge with 1000 LD50 of the guinea pig-adapted Ebola virus.
[b]Data for all animals that died (numbers of animals are shown in parentheses).
[c]Survival rate on day 28 after challenge.
[d]N/A: not applicable.

TABLE 4

Summary of ELISA Result of Anti-Ebola-GP McAbs

| | | Antigen | | | | | |
|---|---|---|---|---|---|---|---|
| McAb | Isotype | eVLPs | eGP1,2 ΔTm | sGP 1-295aa | Rf-GP1 sub-f-D 157-369aa | Mucin domain 333-458aa | GP1 1-501aa |
| 1H3 | IgG2a,κ | + | + | + | − | − | + |
| 2G4 | IgG2b,κ | + | + | − | − | − | − |
| 4G7 | IgG2a,κ | + | + | − | − | − | + |
| 5D2 | IgG2a,κ | + | + | − | + | + | + |
| 5E6 | IgG2a,λ | + | + | − | − | + | + |
| 7C9 | IgG2a,κ | + | + | − | ± | + | + |
| 7G4 | IgG1,κ | + | + | − | − | ± | + |
| 10C8 | IgG2a,κ | + | + | − | − | ± | + |

Antigens (0.3 μg/well) were coated in 96 well microtitre plate then blocking with 2% skim milk. Serial dilutions of each MAb were applied to the plate followed by HRP-conjugated goat anti-mouse IgG. After incubabing with substrate, the asorbance awas read at OD405. Cut off was 2X background.

TABLE 5

Prolonged survival seen in McAb-treated Guinea pigs

| Treatment[a] | Mean time to death[b] | Student's t-test |
|---|---|---|
| MAb 1H3 | 11.7 ± 2.18 (n = 5) | p = 0.0181 |
| MAb 2G4 | 11.5 ± 1.50 (n = 2) | N/A[c] |
| MAb 4G7 | 10.5 ± 1.50 (n = 2) | N/A[c] |
| MAb 5D2 | 9.4 ± 1.02 (n = 5) | p = 0.0244 |
| MAb 5E6 | 10.8 ± 1.47 (n = 5) | p = 0.0092 |
| MAb 7C9 | 9.6 ± 0.80 (n = 5) | p = 0.0056 |
| MAb 7G4 | 9.6 ± 0.80 (n = 5) | p = 0.0056 |
| MAb 10C8 | 9.4 ± 1.20 (n = 5) | p = 0.0428 |
| PBS | 7.67 ± 0.75 (n = 6) | N/A[c] |

[a]Guinea pigs were intraperiotoneally treated with 5 mg of the MAb as showed in the table on day 1 after challenge with 1000 LD$_{50}$ of the guinea pig-adapted Ebola virus.
[b]Data for all animals that died (numbers of animals are shown in parentheses).
[c]N/A: not applicable.

TABLE 6

Protective efficacy of MAbs in guinea pigs

| Treatment | Day of treatment[a] | Meantime to death[b] | No. of survival/Tatal[c] |
|---|---|---|---|
| Cocktail of 4G7(2 mg) + 1H3(1.5 mg) + 2G4(1.5 mg) | −1 | 11.17 ± 3.09 (n = 3) | 3/6 |
| Cocktail of 4G7(2 mg) + 1H3(1.5 mg) + 2G4(1.5 mg) | +1 | 7.92 ± 0.42 (n = 3) | 3/6 |
| Cocktail of 4G7(2 mg) + 1H3(1.5 mg) + 2G4(1.5 mg) | +2 | N/A[d] | 6/6 |
| Cocktail of 4G7(2 mg) + 1H3(1.5 mg) + 2G4(1.5 mg) | +3 | 11.17 ± 3.09 (n = 3) | 4/6 |
| PBS | +2 | 6.58 ± 0.59 (n = 6) | 3/6 |

[a]Guinea pigs were intraperiotoneally treated with the MAbs as showed dose in the table on the indicated days before or after challenge with 1000 LD50 of the guinea pig-adapted Ebola virus.
[b]Data for all animals that died (numbers of animals are shown in parentheses).
[c]Survival rate on day 28 after challenge.
[d]N/A: not applicable.

The invention claimed is:

1. A monoclonal antibody that binds Ebola glycoprotein comprising a light chain variable region comprising the amino acid sequence deduced from the nucleic acid molecule as set forth in SEQ ID NO:4 and a heavy chain variable region comprising the amino acid sequence deduced from the nucleic acid molecule as set forth in SEQ ID NO:3.

2. A method of preparing a chimeric antibody that binds Ebola glycoprotein comprising:
providing an expression vector comprising a nucleic acid molecule encoding a constant region domain of a human light chain genetically linked to a nucleic acid molecule encoding a light chain variable region comprising the nucleic acid molecule as set forth in SEQ ID No: 4; and
providing an expression vector comprising a nucleic acid molecule encoding a constant region domain of a human heavy chain genetically linked to a nucleic acid molecule encoding a heavy chain variable region comprising the amino acid sequence deduced from the nucleic acid molecule as set forth in SEQ ID No.3;
expressing the expression vectors in a suitable host; and
recovering the chimeric antibody that binds Ebola glycoprotein from said host.

3. A method of preparing a chimeric antibody that binds Ebola glycoprotein comprising:
providing an expression vector comprising a nucleic acid molecule encoding a constant region domain of a human light chain genetically linked to a nucleic acid molecule encoding a light chain variable region comprising the nucleic acid molecule as set forth in SEQ ID No:4; and a nucleic acid molecule encoding a constant region domain of a human heavy chain genetically linked to a nucleic acid molecule encoding a heavy chain variable region comprising the amino acid sequence deduced from the nucleic acid molecule as set forth in SEQ ID No:3;
expressing the expression vector in a suitable host; and
recovering the chimeric antibody that binds Ebola glycoprotein from said host.

4. A pharmaceutical composition comprising the monoclonal antibody of claim 1 and a pharmaceutically acceptable excipient or carrier.

* * * * *